United States Patent [19]

Ziegenhorn et al.

[11] Patent Number: 4,486,531

[45] Date of Patent: Dec. 4, 1984

[54] METHOD AND REAGENT FOR THE DETERMINATION OF β-LIPOPROTEIN

[75] Inventors: Joachim Ziegenhorn, Starnberg; Knut Bartl, Wilzhofen; Max Brandhuber, Weilheim, all of Fed. Rep. of Germany

[73] Assignee: Boehringer Mannheim GmbH, Mannheim-Waldhof, Fed. Rep. of Germany

[21] Appl. No.: 489,139

[22] Filed: May 4, 1983

Related U.S. Application Data

[63] Continuation of Ser. No. 233,345, Feb. 11, 1981, abandoned.

[30] Foreign Application Priority Data

Feb. 29, 1980 [DE] Fed. Rep. of Germany ....... 3007764

[51] Int. Cl.$^3$ ................. G01N 33/68; G01N 33/92; C12Q 1/44; C12Q 1/60
[52] U.S. Cl. ....................... 435/19; 436/13; 436/15; 436/17; 436/71; 436/177; 436/175; 435/810; 435/11
[58] Field of Search ............ 435/11, 19, 810; 23/909, 230 B; 424/2, 4; 252/408 R; 436/71, 175, 177, 13, 15, 17

[56] References Cited

U.S. PATENT DOCUMENTS

| | | | |
|---|---|---|---|
| 4,039,285 | 8/1977 | Teipel | 23/230 B |
| 4,066,508 | 1/1978 | Rauscher et al. | 435/19 |
| 4,110,077 | 8/1978 | Klein et al. | 23/230 B |
| 4,309,364 | 1/1982 | Bentzen et al. | 242/204 |

FOREIGN PATENT DOCUMENTS 0159158 12/1980 Japan ..................... 435/11

OTHER PUBLICATIONS

Kim et al., "Nature of the Interaction of Dextran Sulfate with High and Low Density Lipoproteins in the Presence of Ca$^{2+}$", *Journal of Biological Chemistry*, (10–1979), pp. 9621–9626.

Allen et al., "An Enzymatic and Centrifugal Method for Estimating High–Density Lipoprotein Cholesterol", *Clinical Chemistry*, vol. 25, (2), (1979), pp. 325–327.

Hawley, *The Condensed Chemical Dictionary*, Van Nostrand Reinhold Co., N.Y., (1974), pp. 190, 191, 233 and 516.

*Primary Examiner*—Thomas G. Wiseman
*Assistant Examiner*—John Tarcza
*Attorney, Agent, or Firm*—Felfe & Lynch

[57] ABSTRACT

The present invention provides a process for the direct turbidimetric determination of β-lipoproteins (LDL) in body fluids by precipitation with polyanions and divalent cations, wherein the precipitation is carried out in the presence of a complex former at a pH value of from 7 to 9.

The present invention also provides a reagent for the direct turbidimetric determination of β-lipoproteins (LDL) in body fluids, comprising a polyanion, a salt of a divalent metal, a complex former and a substance buffering at pH 7 to 9. .

23 Claims, 1 Drawing Figure

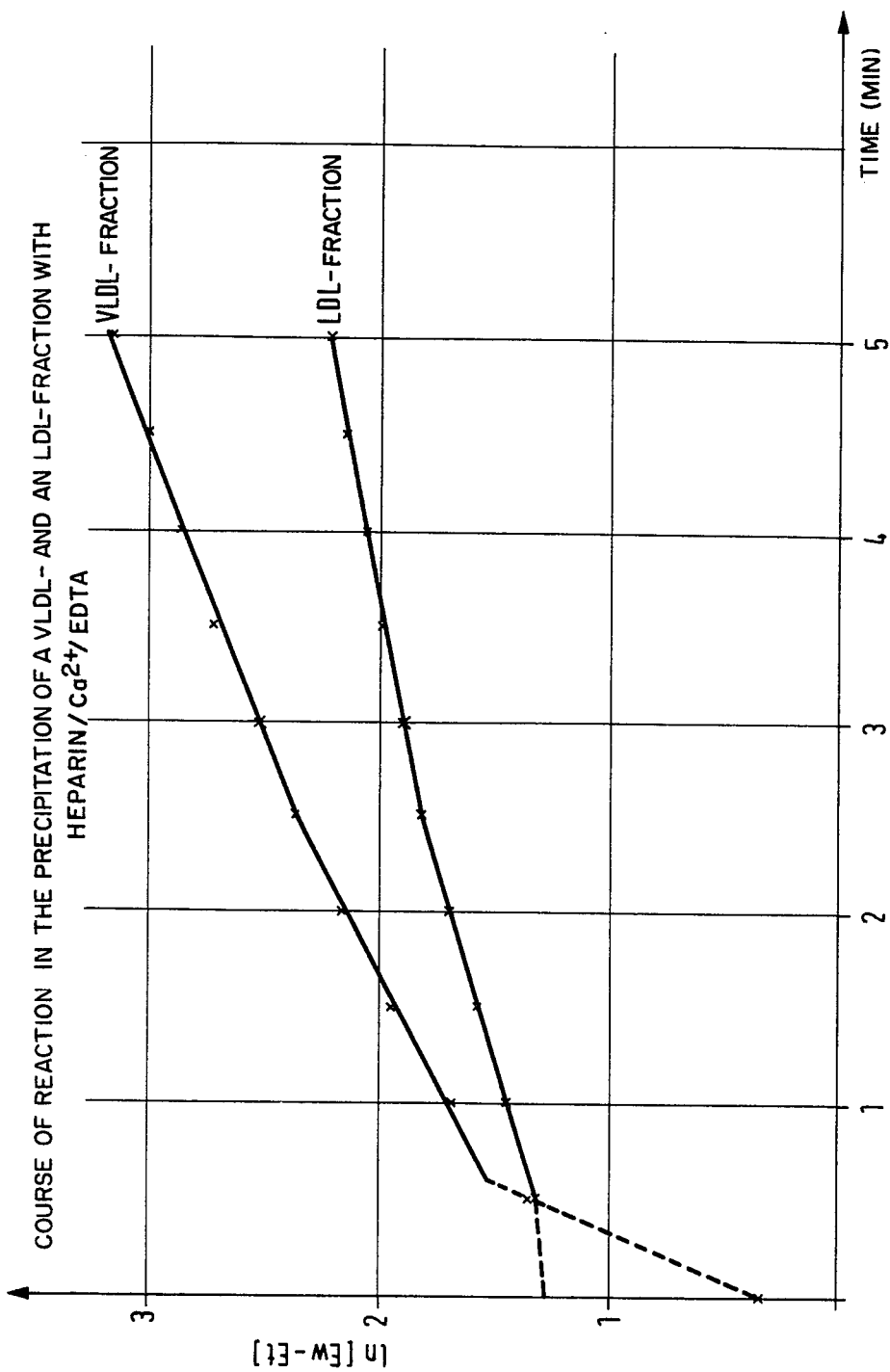

METHOD AND REAGENT FOR THE DETERMINATION OF β-LIPOPROTEIN

This application is a continuation of application Ser. No. 233,345, filed 2/11/81 now abandoned.

This invention relates to a method and a reagent for the determination of the beta-lipoprotein fraction (low density lipoprotein (LDL)) in body fluids.

Hypercholesterolaemia and hypertriglyceridaemia favor the development of atherosclerosis and of cardiac infarction. The determination of cholesterol and of triglycerides in serum belong, therefore, to the most frequently performed tests in routine clinical-chemical laboratories.

Numerous investigations into fat metabolism have resulted in the conclusion that the individual coronary risk can be better assessed when there is determined not only the change of the triglyceride and cholesterol ledvel but also the fundamental pathological displacement in the lipoprotein picture (see Münch. med. Wschr., 121, 1639/1979).

The known plasma lipoproteins contain a proportion of protein, phospholipids, cholesterol and triglycerides of varying magnitude. On the basis of their behavior (differing density), they can be subdivided in an analytical centrifuge into three different classes:
- pre-β-lipoproteins=VLDL (very low density lipoprotein)
- β-lipoprotein=LDL (low density lipoprotein)
- α-lipoprotein=HDL (high density lipoprotein).

The investigation of the function of the lipoproteins showed that LDL, among the lipoproteins, represents the decisive atherogenic component, an increase of which in the blood results in an increased risk of coronary heart disease. The early recognition and combating of this condition is of great importance. Therefore, there is a need for a practical process for the quantitative determination of the LDL concentration in serum and plasma.

Hitherto, for the determination of the LDL lipoprotein fraction, essentially four methods have been used which, however, suffer from certain disadvantages:

1. Ultracentrifuging.

This process is not suitable for use in a routine laboratory since special equipment is necessary and the carrying out of the process requires an extremely careful working procedure and a very large expenditure of time (2×20 hours at 105,000 g). Consequently, the use of this analytical process has hitherto been limited to the medical research laboratory.

2. Precipitation reaction.

The LDL content can also be determined by fractional precipitation with polyanions, for example heparin sodium or dextran sulphate, and divalent cations, for example calcium, manganese or magnesium cations. The lipoproteins can be precipitated out, with increasing concentration of the polyanions, in the following sequence: VLDL, LDL and HDL. However, this process requires two working steps and is thus not practical and cannot be automated: VLDL is separated off in a first precipitation step and subsequently, by increasing the concentration of the precipitation agent, the LDL lipoprotein fraction is precipitated and determined turbidimetrically (see H. Okabe, 10th Int. Congr. of Clin. Chem., Mexico, 1978).

3. Determination of the LDL concentration by means of the Friedewald formula.

In the case of this process, the triglyceride, cholesterol and HDL-cholesterol content of the sample are determined and the content of LDL cholesterol calculated therefrom according to Friedewald's process (see Clin. Chem., 18, 499/1972). This laborious process is also not practical.

4. Qualification by electrophoretic separation and polyanion precipitation.

This process is also time-consuming and requires the use of an electrophoresis apparatus, as well as of a densitometer for the evaluation (see Lab. med., 1, 145/1977).

Therefore, it is an object of the present invention to provide a practical process which can be automated and with which LDL can be determined directly in a routine laboratory.

Thus, according to the present invention, there is provided a process for the direct turbidimetric determination of the β-lipoproteins (LDL) in body fluids, such as serum or plasma, by precipitation with polyanions and divalent cations from an aqueous solution, wherein the precipitation is carried out in the presence of a complex former at a pH value of from 7 to 9.

The present invention is based upon the discovery of the surprising fact that LDL can be selectively and practically quantitatively precipitated in the presence of VLDL and HDL and can be determined turbidimetrically when the precipitation is carried out with the combination of complexing agent, polyanion and cation. This is surprising since, according to previously published investigations, when precipitating LDL, VLDL is always coprecipitated if it has not been previously separated off (see M. Burstein, H. R. Scholnick, "Protides of the biological fluids", ed. Peeters, pp. 21–28/1972; Arztl. Lab., 23, 101–110/1977). However, according to the present invention, it is, surprisingly, possible selectively to precipitate LDL in such a manner that a kinetic measurement, i.e. a measurement within a predetermined period of time, can be carried out. At the same time, the error in comparison with the known processes of joint precipitation of VLDL and LDL is substantially reduced.

The complex formers used according to the present invention are to be understood to be compounds which are capable of forming complexes, i.e. compounds of a comparatively high order which are formed by combination of molecules. The polyligands have proved to be especially useful, for example the tri-, tetra- and hexaligands, the hexaligands being preferred, for example aminopolycarboxylic acids, such as ethylenediaminetetraacetic acid (EDTA), nitrilotriacetic acid (NTA) and diethylenetriamine-pentaacetic acid.

The complex former is generally used in an amount of from about 1 to 35 g./liter and preferably of from 5 to 25 g./liter.

The cations used according to the present invention are in the form of salts of divalent cations with an anion which does not disturb the reaction, divalent cations of the alkaline earth metal group being preferred. Examples of other divalent cations which can be used include manganese and cobalt. Calcium is especially preferred.

According to a preferred embodiment of the process of the present invention, the cations and complex former are first reacted together to give a salt-like complex which, possibly after previous isolation, can be used for the process according to the present invention. If the complex is first separated out from the solution in which it is formed, it admittedly does not matter whether the components are used in stoichiometric amount since a component which is present in excess and does not participate in the complex formation is separated off with the solvent. Preferably, however, the cations and complex former are used in stoichiometric amount. This also applies when complex formation is carried out directly in the solution to be investigated. Since it is frequently desirable to have an excess of cation present during the precipitation, in the case of this embodiment it is preferable first to add the complex former and the cations in stoichiometric amount and then to introduce an excess of cations after complex formation has taken place. The concentration of cations in the solution is preferably from 0.01 to 0.3M and more preferably from 0.08 to 0.15M. The cations may be used, for example, in the form of nitrates, acetates, sulphates or halides, the chlorides being preferred.

The third substance necessary for the process according to the present invention is a polyanion. Examples of suitable polyanions include sulphated polysaccharides, such as heparin, dextran sulphate and mepesulphate and phosphotungstates. Heparin is preferred, especially in the form of the sodium salt. Polysulphates can also be used, for example sodium polyethanolsulphonate and similar compounds. The preferred polyanion concentration is generally from 0.005 to 0.5%.

According to a preferred embodiment of the process of the present invention, an ester-splitting enzyme is also added, examples of appropriate ester-splitting enzymes including the lipases and the esterases, a lipase from *Rhizopus arrhizus* or a cholesterol esterase being especially preferred. The addition of such an ester-splitting enzyme increases the exactitude of the process since errors due to coprecipitated VLDL can thereby be eliminated. Without the use of an ester-splitting enzyme, a lag phase frequently occurs so that measurement can only be commenced after 1 to 2 minutes. This lag phase disappears in the presence of an ester-splitting enzyme so that the period of determination can thereby also be shortened. Therefore, in the case of this preferred embodiment of the present invention, not only the practicability but also the sensitivity are increased.

The turbidimetric measurement can be carried out preferably kinetically, the possibility of carrying out the measurement kinetically, i.e., within a predetermined time interval, thereby being especially advantageous.

The adjustment of the pH to a value of from 7 to 9 can be carried out in known manner, preferably with the use of a buffer. In principle, all substances buffering in the given range can be used, examples of appropriate buffers including imidazole/HCl, as well as tra/HCl, tris/HCl being preferred.

The present invention also provides a reagent for the direct turbidimetric determination of β-lipoproteins (LDL) in body fluids, such as serum or plasma, said reagent comprising a polyanion, a salt of a divalent metal, a complex former and a substance buffering at pH 7 to 9.

With regard to the individual components of the reagent and the amounts thereof, the statements made hereinbefore in connection with the process also apply. Therefore, the reagent according to the present invention preferably also contains an ester-splitting enzyme, especially a lipase and more especially a lipase from *Rhizopus arrhizus*.

The reagent according to the present invention preferably contains the complex former already in a complexed state with a divalent metal, i.e. the cation. The preferred amount of complex salt is 2 to 25 g., referred to the preparation of a 1 liter amount of reagent. The polyanion is preferably present in an amount of from 0.02 to 0.5%. If the preferred polyanion heparin sodium is used, then this corresponds to 30,000 to 750,000 USP, again referred to the amount required for the preparation of 1 liter of liquid reagent.

With regard to the buffer substance, there again apply the statements made above with regard to the process. The buffer substance is preferably present in an amount such that the concentration thereof in the liquid reagent is from 100 to 150 mMol/liter and more preferably from 120 to 140 mMol/liter. This applies especially for the preferred tris/HCl buffer.

If an ester-splitting enzyme is present, the amount thereof is preferably from 100 to 6000 U/liter of dissolved reagent and more preferably 500 to 2000 U.

Consequently, a preferred reagent according to the present invention has the following composition:

0.02 to 0.5% by weight heparin sodium (30,000 to 750,000 USP/liter), dextran sulphate or polyphosphotungstic acid, 2 to 25 g./liter of a complex salt of calcium and ethylenediamine-tetraacetic acid, 15 to 50 mMol/liter calcium chloride, 100 to 150 mMol/liter tris/HCl, pH 7 to 9 and optionally 100 to 6000 and preferably 500 to 2000 U/liter of ester-splitting enzyme.

Equally good results are obtained with a reagent of the above composition, regardless of whether use is made of heparin sodium or of an equivalent amount of dextran sulphate.

According to the present invention, the VLDL precipitation can be neglected during the measuring interval (see the following Table 1).

In the accompanying drawing, the VLDL and the LDL precipitation reaction under the conditions of the following Example 1 are plotted semilogarithmically.

It can be seen that completely different reaction rate constants are obtained. The result of this is that, according to the present invention, both courses of reaction can be differentiated.

In the case of the known process in which LDL and VLDL are coprecipitated by means of the addition of heparin and calcium, the error, referred to the LDL fraction, is 30%. In contradistinction thereto, according to the present invention, even in the embodiment without the ester-splitting enzyme, this error is reduced to less than 8%.

The process and reagent according to the present invention are thus characterized by the fact that, for the first time, LDL can be specifically determined by a single reaction which is easy to carry out. Slight disturbances by possible coprecipitated VLDL can be prevented by the addition of an esterase. By means of the turbidity measurement, which is preferably carried out according to the principle of the kinetic fixed time method, the following advantages are obtained:

1. A blank value determination is unnecessary.
2. Kinetic fixed time methods are especially suitable for carrying out the determination using modern automatic analyzers. This process is, therefore, readily adaptable to the analysis devices available in modern routine laboratories.

The measurement value used is the increase in extinction due to the turbidity in the measurement time interval. This extinction increase can be measured preferably by the kinetic process. The test may be evaluated by means of a calibrated curve produced with standard samples.

Without sample predilution, the present invention enables LDL values of up to about 600 mg./dl. to be determined.

The following Examples are given for the purpose of illustrating the present invention. The salt complex used in all of the Examples was prepared by means of the following process:

36 g. Ethylenediamine-tetraacetic acid are dissolved in 400 ml. double distilled water. After filtration, 16 g. calcium chloride are added to this solution. After stirring for 15 minutes at ambient temperature, the suspension is kept for one day at 4° C. and subsequently suction filtered through a glass filter, washed free of chloride and dried.

EXAMPLE 1

The determination described in the following was carried out by the kinetic fixed time process, using the following reagents:
Reagent 1:
 124 mMol/liter tris/HCl, pH 7.5
 151,000 USP/liter heparin
 20 g./liter Ca$^{++}$/EDTA (salt complex)
Reagent 2:
 0.68 Mol/liter calcium chloride
Test formulation:
 measurement wavelength: Hg 365 nm; layer thickness of
 the cuvette: 1 cm.; measurement temperature: 25° C.

2.5 ml. of Reagent 1 are pipetted into a cuvette, 0.05 ml. of sample is added thereto, mixed and the reaction is commenced with 0.1 ml. of Reagent 2. $E_1$ is read off 90 seconds after the start and $E_2$ 300 seconds after the start. The so obtained extinction difference $\Delta E = E_2 - E_1$ is used for the evaluation.

Evaluation:

The measured extinction difference is referred to an LDL concentration reference curve produced with the use of one or more standard samples.

If, in the case of this Example, there is used, on the one hand, a purified VLDL and, on the other hand, a VLDL-free serum and the extinctions measured at the different times are evaluated semilogarithmically, then there are obtained the different reaction kinetics for VLDL and LDL given in the accompanying drawing. The different slopes clearly show this.

EXAMPLE 2 (WITH THE ADDITION OF LIPASE)

Measurement took place by the fixed time process.
Reagent 1:
 124 mMol/liter tris/HCl, pH 7.5
 151,000 USP/liter heparin
 20 g./liter Ca-EDTA
 1500 U/liter lipase
Reagent 2:
 0.68 mol/liter calcium chloride The test formulation is analogous to that described in Example 1. 2.5 ml. of Reagent 1 are pipetted into the cuvette, 0.05 ml. of sample is added thereto, mixed and the reaction commenced with 0.1 ml. of Reagent 2. $E_1$ is measured 30 to 90 seconds after the start of the reaction and $E_2$ 300 seconds after the start. The extinction difference $\Delta E = E_2 - E_1$ thus obtained is used for the evaluation.

For the purpose of comparison, the determination was repeated according to the known method 2 described above. The results obtained are given in the following Table 1:

TABLE 1

| | Influence of different precipitation reagents on the precipitation of VLDL and LDL | | |
|---|---|---|---|
| | heparin/Ca$^{++}$ $\Delta E$ (90–300 seconds) | heparin/Ca$^{++}$/ EDTA, $\Delta E$ (90–300 seconds) | heparin/Ca$^{++}$/ EDTA/lipase $\Delta E$ (90–300 seconds) |
| VLDL fraction | 0.014 | 0.006 | 0.000 |
| % error due to VLDL, referred to LDL | 30 | 7 | 0 |

EXAMPLE 3

The procedure described in Example 2 was repeated except that use was made of a reagent with the following composition:
Reagent 1:
 124 mMol/liter tris/HCl, pH 7.5
 0.1% polyphosphotungstic acid
 24 g./liter Ca/EDTA
 1500 U/liter lipase
Reagent 2:
 0.23 mol/liter calcium chloride.

The results obtained correspond to those of Example 2.

It will be understood that the specification and examples are illustrative, but not limitative, of the present invention and that other embodiments within the spirit and scope of the invention will suggest themselves to those skilled in the art.

What is claimed is:

1. A method for the direct turbidimetric determination of beta-lipoproteins (LDL) in body fluids, in the presence of pre-beta-lipoproteins (VLDL) and alpha-lipoproteins (HDL) consisting essentially of adding a test sample, to a mixture of 0.005% to 0.5% of a polyanion and 1 to 35 grams/l of a chelating agent for a divalent cation that is different than the polyanion, said mixture and sample being at a ph value of from 7 to 9; adding 0.01 to 0.3 m of the divalent cation to cause turbidity to form and, thereafter, measuring the turbidity formed to determine the quality of the LDL.

2. Method as claimed in claim 1 wherein an ester splitting enzyme is also added in carrying out the precipitation.

3. Method as claimed in claim 2 wherein a lipase from *Rhizopus arrhizus* is used as the ester splitting enzyme.

4. Method as claimed in claim 1 wherein said complex former is a poly-ligand.

5. Method as claimed in claim 4 wherein said polyligand is a hexaligand.

6. Method as claimed in claim 5 wherein the hexaligand is ethylenediamine-tetraacetic acid (EDTA).

7. Method as claimed in claim 1 wherein the cation used is an alkali earth metal cation.

8. Method as claimed in claim 1 wherein the cation used is a manganese cation.

9. Method as claimed in claim 1 wherein the cation used is a cobalt cation.

10. Method as claimed in claim 1 wherein the cation and complex former are used in equal molar amounts.

11. Method as claimed in claim 1 wherein the complex former and the cation are first reacted with one another and the salt-like complex formed is in carrying out the precipitation.

12. Method as claimed in claim 1 wherein heparin sodium, polyphosphotungstic acid or dextran sulphate is used as the polyanion.

13. Method as claimed in claim 1 wherein the determination is carried out kinetically by measurement in a predetermined period of time.

14. Method as claimed in claim 1 wherein tris(hydroxymethyl)-aminomethane hydrochloride triethanolamine hydrochloride or imidazole hydrochloride is used as a buffer to achieve the desired pH.

15. Reagent for the direct turbidimetric determination of beta-lipoproteins (LDL) in body fluids, in the presence of per-beta-lipoproteins (VLDL and alpha-lipoproteins (HDL) said reagent consisting essentially of —0.005% to 0.5% of a polyanion, 0.01 to 0.3 m of a salt of a divalent metal, and 1 to 35 grams per liter of a chelating agent for the divalent cation; and a buffer substance buffering at pH 7 to 9.

16. Reagent as claimed in claim 15 additionally containing an ester-splitting enzyme.

17. Reagent as claimed in claim 16 wherein the ester splitting enzyme is a lipase from *Rhizopus arrhizus*.

18. Reagent as claimed in claim 15 wherein the complex former is a poly-ligand.

19. Reagent as claimed in claim 18 wherein the poly-ligand is a hexaligand.

20. Reagent as claimed in claim 19 wherein the hexaligand is ethylenediamine-tetraacetic acid.

21. Reagent for the direct turbidimetric determination of beta-lipoproteins (LDL) in body fluids, which reagent comprises
  0.02 to 0.5% by weight heparin sodium 30,000 to 75,000 USP, dextran sulphate or polyphosphotungstic acid;
  2 to 35 grams per liter of a complex salt of calcium ions and ethylenediamine-tetraacetic acid;
  15 to 50 mMol/liter calcium chloride; and
  100 to 150 mMol/liter tris(hydroxymethyl)-aminomethane hydrochloride buffer having a pH 7 to 9.

22. Reagent as claimed in claim 21 additionally containing 100 to 6000 U/liter of an ester splitting enzyme.

23. Reagent as claimed in claim 22 wherein the ester splitting enzyme is present in an amount of from 500 to 2000 U/liter.

* * * * *